United States Patent
Anderson et al.

(10) Patent No.: US 6,520,026 B1
(45) Date of Patent: Feb. 18, 2003

(54) METHOD FOR MAKING AND TESTING THERMOCOMPRESSION BONDS

(75) Inventors: Lynda L. Anderson, Saugerties, NY (US); Gilles Granier, Vailhauques (FR); Robert E. Mahoney, Jr., Poughkeepsie, NY (US); Bruce E. Moore, Poughkeepsie, NY (US); Kenneth A. Scea, Poughkeepsie, NY (US); Kent D. Waddell, West Hurley, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/433,027

(22) Filed: Nov. 3, 1999

(51) Int. Cl.[7] .............................................. G01N 3/08
(52) U.S. Cl. ..................................................... 73/827
(58) Field of Search ......................... 73/827, 828, 830, 73/834, 835

(56) References Cited

U.S. PATENT DOCUMENTS

| | | | | |
|---|---|---|---|---|
| 2,473,517 A | * | 6/1949 | Freedman | 73/150 A |
| 3,607,432 A | * | 9/1971 | Johnson | 136/120 R |
| 3,641,660 A | * | 2/1972 | Adams et al. | 228/102 |
| 3,715,070 A | | 2/1973 | Shibata | 228/44 |
| 3,819,104 A | | 6/1974 | Lang | 228/3 |
| 3,842,235 A | * | 10/1974 | Opprecht | 219/83 |
| 3,891,822 A | * | 6/1975 | Laub et al. | 219/85.18 |
| 3,950,631 A | * | 4/1976 | Schmidt et al. | 219/107 |
| 4,429,458 A | | 2/1984 | Shibata | 19/879 |
| 5,275,058 A | * | 1/1994 | Pham et al. | 324/538 |
| 5,343,011 A | * | 8/1994 | Fujii et al. | 219/109 |
| 5,389,743 A | * | 2/1995 | Simila et al. | 174/262 |
| 5,591,920 A | * | 1/1997 | Price et al. | 228/4.5 |
| 5,645,738 A | * | 7/1997 | Cecil | 219/110 |
| 6,078,028 A | * | 6/2000 | Cooper et al. | 219/270 |

* cited by examiner

*Primary Examiner*—Max Noori
*Assistant Examiner*—Lilybett Martir
(74) *Attorney, Agent, or Firm*—Floyd A. Gonzalez

(57) ABSTRACT

A method for making and testing the thermal compression bond between a wire and a contact or terminal lead of a connector wherein the wire and contact/terminal lead are positioned between opposing electrodes, and a direct current is passed through the electrodes, wire and contact/terminal lead to make a direct attach thermocompression bond. Sample bonds are subjected to a peel test to determine if the thermocompression bonds are within specification. The peel test includes securing the contact/terminal lead, bend the wire 90 degrees from the contact/terminal lead, and applying force to the wire at a constant rate of pull until thermocompression bond is broken and the wire is separated from the contact/terminal lead. The peel force required to break the bond is then compared to a standard to determine if the thermocompression bonds are within determined specifications. Additionally, an axial pull test may also be performed.

25 Claims, 6 Drawing Sheets

ACCEPTABLE

ACCEPTABLE

UNACCEPTABLE

ACCEPTABLE

UNACCEPTABLE

UNACCEPTABLE

METHOD FOR MAKING AND TESTING THERMOCOMPRESSION BONDS

The present invention is related to thermocompression bonding of wire using opposing electrodes, and is more particularly related to testing such thermal compression bonding.

BACKGROUND OF THE INVENTION

Prior techniques for attaching wire to straddle mount connectors required the use of a printed circuit card which was used as the interface to the connector. The wires were attached via solder to reflow to the card. On larger gauge wires (26 AWG+), a new technique had to be developed since printed circuit cards would not withstand the high temperatures required to attach the wires without causing delaminations. Resistance welding was considered for directly attaching wires to a connector thereby eliminating the printed circuit card. However, resistance welding requires heating the wire and connector to their melting temperatures, and the melting of all metals in the weld nugget, including coatings and the base metal. In resistance welding, material selection and the thickness of the material is critical. Resistance welding produces a weld which results in a fusion/melting of materials which in turn create alloys of different material characteristics than the original metals such as brittleness due to alloying effects.

SUMMARY OF THE INVENTION

In the present invention, a thermocompression bond is made between a wire and a connection by use of opposing electrodes. The thermocompression bond is made while heating the materials to temperatures below their melting temperatures, and the resulting bond is made by diffusion rather than fusion. The geometry is easy to maintain, and most materials can be adapted. The present invention includes testing the resulting bonds to insure that the bonding setup for the materials is correct. In the invention, a sample of the bonds are subjected to a peel test which includes bending the bonded wire at a right angle to the connector, securing the connector, and applying pulling force at a constant rate of 50 mm (about 2 inches per minute) to the wire until the wire is separated or peeled from the connector. Indications of the bond is defined by wire peel force being greater than 50% of the wire tensile strength with a minimum $C_{pk}$ (capacity index) of 1.5, and with wire deformation being less than 50% of the outside diameter (OD) of the conductor. In addition to the peel test, a pull test may be conducted. The pull test involves an axial pull of the wire at a constant rate of 50 mm (about 2 inches per minute). The pull test shall not show less that 50% of the wire tensile strength with a $C_{pk}$ of 1.5. The data must be normally distributed to calculate a valid $C_{pk}$. The formula for $C_{pk}$ is as follows:

$$C_{pk} = (X^{double\ bar} - LSL)/3\sigma$$

Where:

$X^{double\ bar}$ = the average of all subgroup averages or the grand average,

LSL = the lower specification limit, and

σ = the standard deviation.

Using well known statistical process control on the peel force allows for the desired type of bonding to be continuously achieved.

DESCRIPTION OF THE PREFERRED EMBODIMENT

Figure 1:
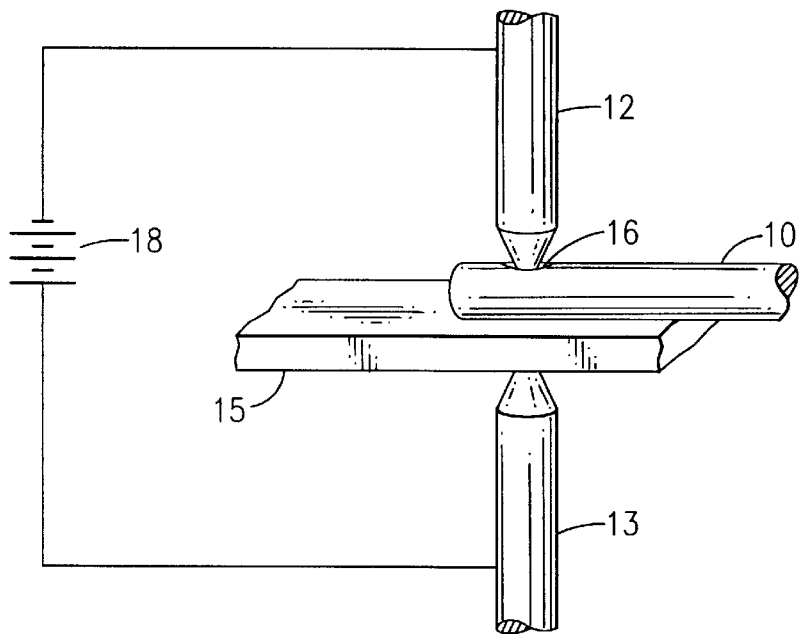
FIG. 1 is an illustrative drawing of a wire being bonded by opposing electrodes to a base component such as a contact or terminal lead of a connector.

FIG. 1 is an illustration of a wire 10 being bonded by opposing electrodes 12 and 13 to a base component such as a contact or a terminal lead (hereinafter referred to as a contact/terminal lead 15) of a connector. The wire 10 is aligned on the contact/terminal lead 15, as will be discussed, and the opposing electrodes 12 and 13 compress the wire 10 onto the contact/terminal lead 15. An electrode impression 16 on the wire 10 is acceptable, however, maximum deformation of the wire 10 is not to exceed 50% of the outside diameter (OD) of the wire. The shape of the deformation must be such that it minimizes stress concentration. The electrode impression 16 must be centered on the wire 10 such that there is undisturbed wire on both ends of the wire. Once the wire 10 is positioned over the contact/terminal lead 15, the electrodes 12 and 13 are connected to a source of DC current 18, and an electric current is passed through the connection to make the thermocompression bond wherein the wire 10 and the contact/terminal lead 15 are heated to temperatures below the melting temperature, and the bond between the two is made by diffusion rather than fusion.

Direct energy or capacitor discharge, inverter type equipment may be used to supply the dc current. The equipment includes electronic controls which allow precise control of bonding time and includes a current and a welding head that maintains the electrode clamping force without deforming the wire. Electronic monitoring of bonding parameters with feedback controls is provided for process control of the bonding operation. The equipment further may maintain a constant electrode temperature.

Figure 2A:
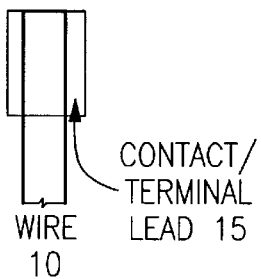
FIGS. 2a, 2b and 2c are illustrations of acceptable and unacceptable wire alignments with a contact or terminal lead of a connector.
Figure 2B:
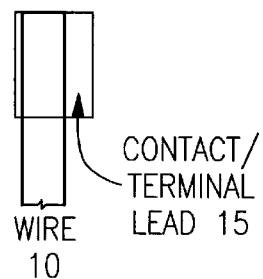
Figure 2C:
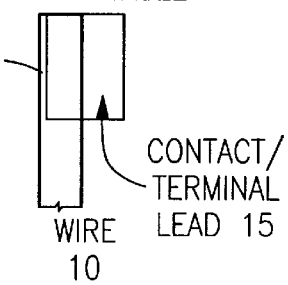
Figure 3A:
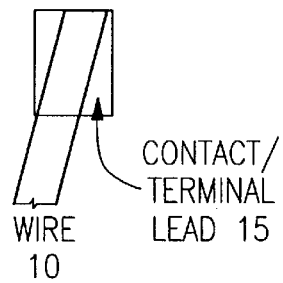
FIGS. 3a, 3b and 3c are illustrations of acceptable and unacceptable wire alignments with a contact or terminal lead of a connector.
Figure 3B:
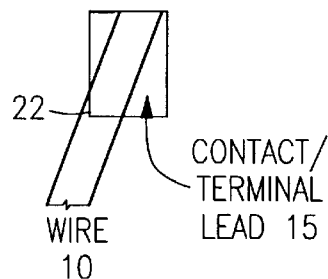
Figure 3C:
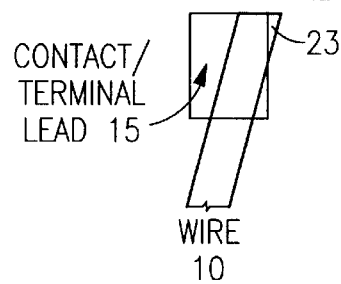

The electrode configuration is aligned such that the entire current passes through the wire 10 and the contact/terminal lead 15. The shape of the electrodes 12 and 13 are such that they minimize the stress concentration zone in the wire deformation area 16. FIGS. 2a and 2b are illustrations of wire alignment on the contact/terminal lead which are acceptable. FIG. 2c is an unacceptable alignment wherein a portion 21 of the wire 10 is not positioned over the contact/ terminal lead 15. FIG. 3*a* is an illustration of wire alignment on the contact/terminal lead which is acceptable. FIGS. 3*b* and 3*c* are illustrations of wire alignment which are unacceptable. In FIG. 3*b* a portion of the wire 22 is not over the contact/terminal lead 15, and in FIG. 3*c,* another portion 23 of the wire 10 is not positioned over the contact/terminal lead 15.

Figure 4A:
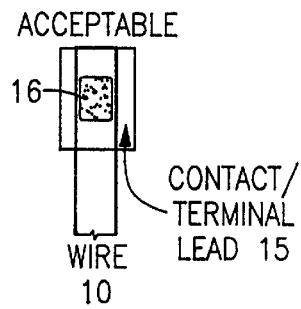
FIGS. 4a, 4b and 4c are illustrations of acceptable and unacceptable wire electrode impressions on a contact or terminal lead of a connector.
Figure 4B:
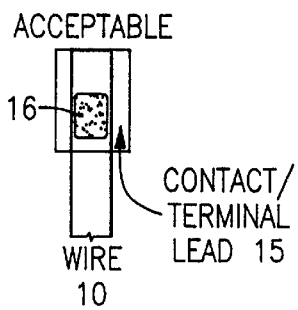
Figure 4C:
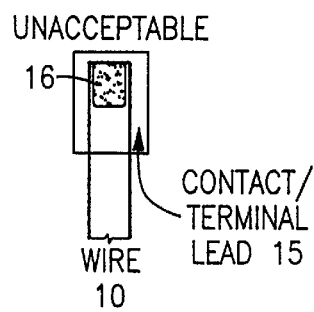
Figure 5A:
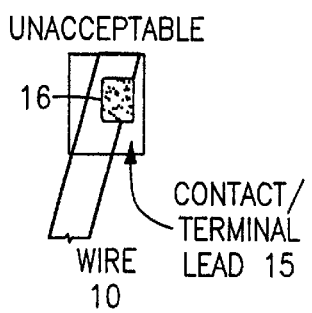
FIGS. 5a, 5b and 5c are illustrations of unacceptable wire electrode impressions on a contact or terminal lead of a connector.
Figure 5B:
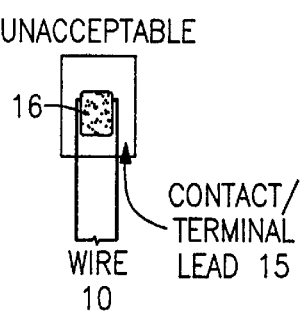
Figure 5C:
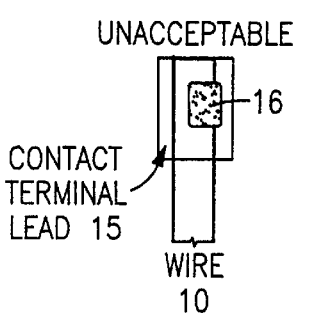

FIGS. 4*a* and 4*b* are illustrations of contact impressions 16 which are acceptable for thermocompression bonding between the wire 10 and the contact/terminal lead 15. In FIGS. 4*a* and 4*b,* there is undisturbed wire 10 at each end of the impression 16 over the contact/terminal lead 15. The impression in FIG. 4*c* is unacceptable because the contact impression 16 is at the end of the wire 10 with no undeformed or undisturbed wire between the impression 16 and the end of the wire 10. FIGS. 5*a,* 5*b* and 5*c* are all illustrations of unacceptable impressions 16 on the wire 10. The impressions 16 of FIGS. 5*a* and 5*c* extend past the sides of the wire 10, and the impression 16 of FIG. 5*b* extends past the end of the wire 10.

Figure 6:
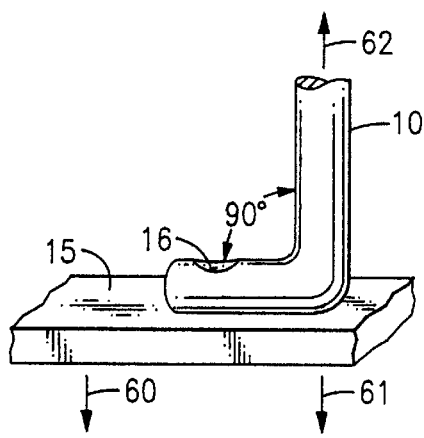
FIG. 6 is an illustration of a pull test of the present invention.

FIG. 6 is an illustration of the peel test of the present invention. Peel tests are performed on a statistical sample of a batch of thermocompression bonds to determine if the bonds of the batch meet the specifications of the bond. First, a statistical sample of the bonds is removed from the batch, and each bond removed is submitted to a peel test. In the peel test, the wire 10 is bent 90 degrees from the contact/terminal lead 15, as shown in FIG. 6. The contact/terminal lead 15 is secured to a test fixture (not shown) at, for instance, the points shown by arrows 60 and 61. A force is then applied, as shown by arrow 62, until the wire 10 is peeled from the contact/terminal lead 15. For annealed copper wire, the specified minimum pull/peel force (also referred to herein as the lower specification limit) is defined in Table 1. For wire sizes not defined in Table 1, and wire other than annealed copper wire, a lower specification limit value can be established by using 50% of the ASTM specified breaking strength for that wire.

TABLE 1

| Wire Size (AWG) | Pull/Peel Force in Pounds | Pull/Peel Force in Newtons |
|---|---|---|
| 26 | 4 | 17.7 |
| 28 | 2.5 | 10.8 |
| 30 | 1.6 | 6.9 |

The peel test involves a 90 degree pull of the wire relative to the contact/terminal lead 15. The peel force 62 is measured at a constant rate of pull of 50 mm, or about 2 inches, per minute. The peel force criteria includes upper and lower control limits based on the process data. To pass the test, the peel force 62 will not be less than 50% of the wire tensile strength with a minimum capability index ($C_{pk}$) of 1.5. The data must be normally distributed to calculate a valid $C_{pk}$. The formula for $C_{pk}$ is as follows:

$$C_{pk} = (X^{double\ bar} - LSL)/3\sigma$$

Where:

$X^{double\ bar}$ = the average of all subgroup averages or the grand average,

LSL = the lower specification limit, and $\sigma$ = the standard deviation.

Figure 8:
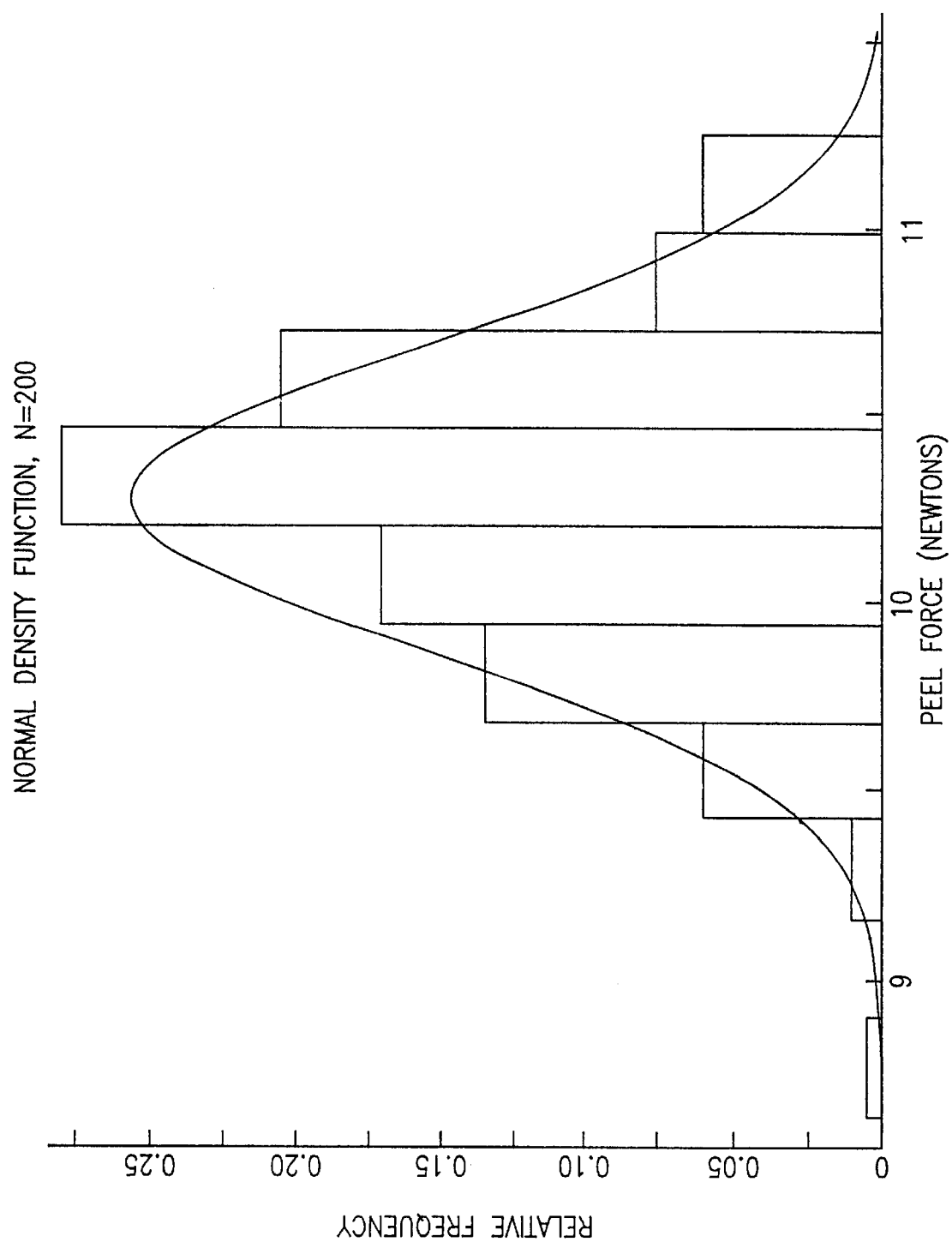
FIG. 8 is a histogram of a acceptable 90 degree peel test data for 30 AWG wire.
Figure 9:
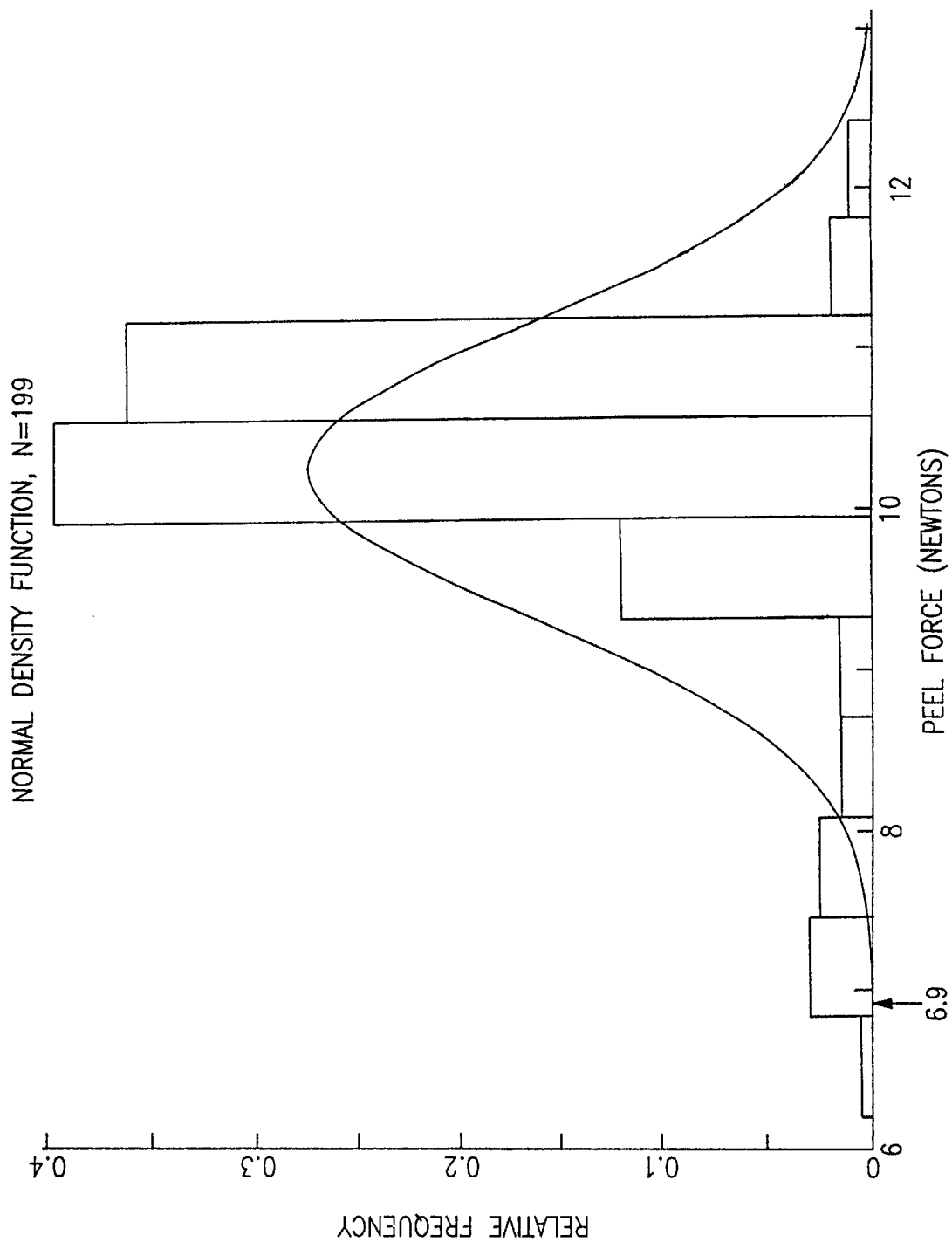
FIG. 9 is a histogram of an unacceptable 90 degree peel test data for 30 AWG wire.

FIG. 8 is a histogram of a sample of acceptable 90 degree peel test data for 30 AWG wire. FIG. 9 is a histogram of a sample of unacceptable 90 degree peel test data for 30 AWG wire.

Figure 7:
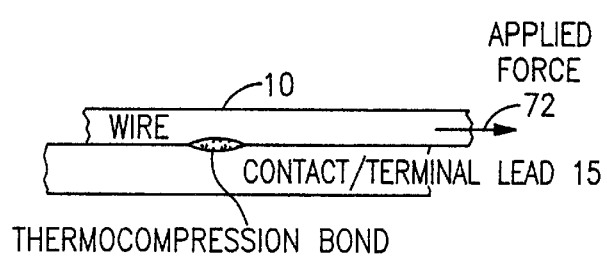
FIG. 7 is an illustration of an axial pull test of the present invention.

In addition to the peel test, the thermocompression bond may be subjected to an axial pull test. The pull test involves an axial pull of the wire 10 at a constant rate of pull of 50 mm (about 2 inches) per minute, as shown in FIG. 7. In the pull test of FIG. 7, the contact/terminal lead 15 is fixed in a test fixture (not shown), and the wire 10 is pulled by an axial pull shown by the arrow 72. To pass the pull test, the thermocompression bond will not break at less than 50% of the wire tensile strength with a $C_{pk}$ of 1.5. The lower specification limit pull force may be the same as shown in Table 1. The data must be normally distributed to calculate a valid $C_{pk}$.

Figure 10:
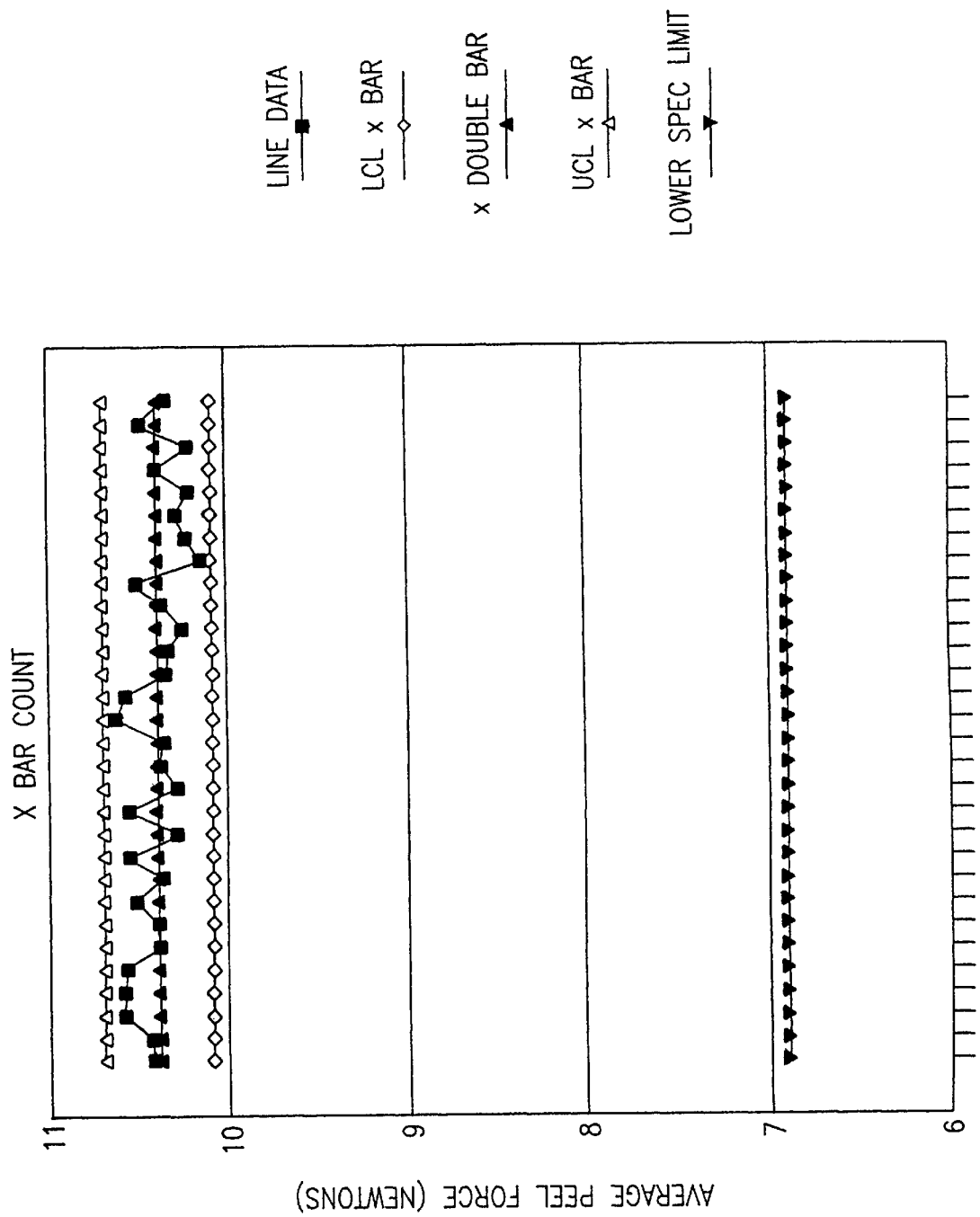
FIG. 10 is a statistical process control chart plotting the peel test which provides for continuously achieving the desired bonding of wire to a contact or terminal lead of a connector.
Figure 11:
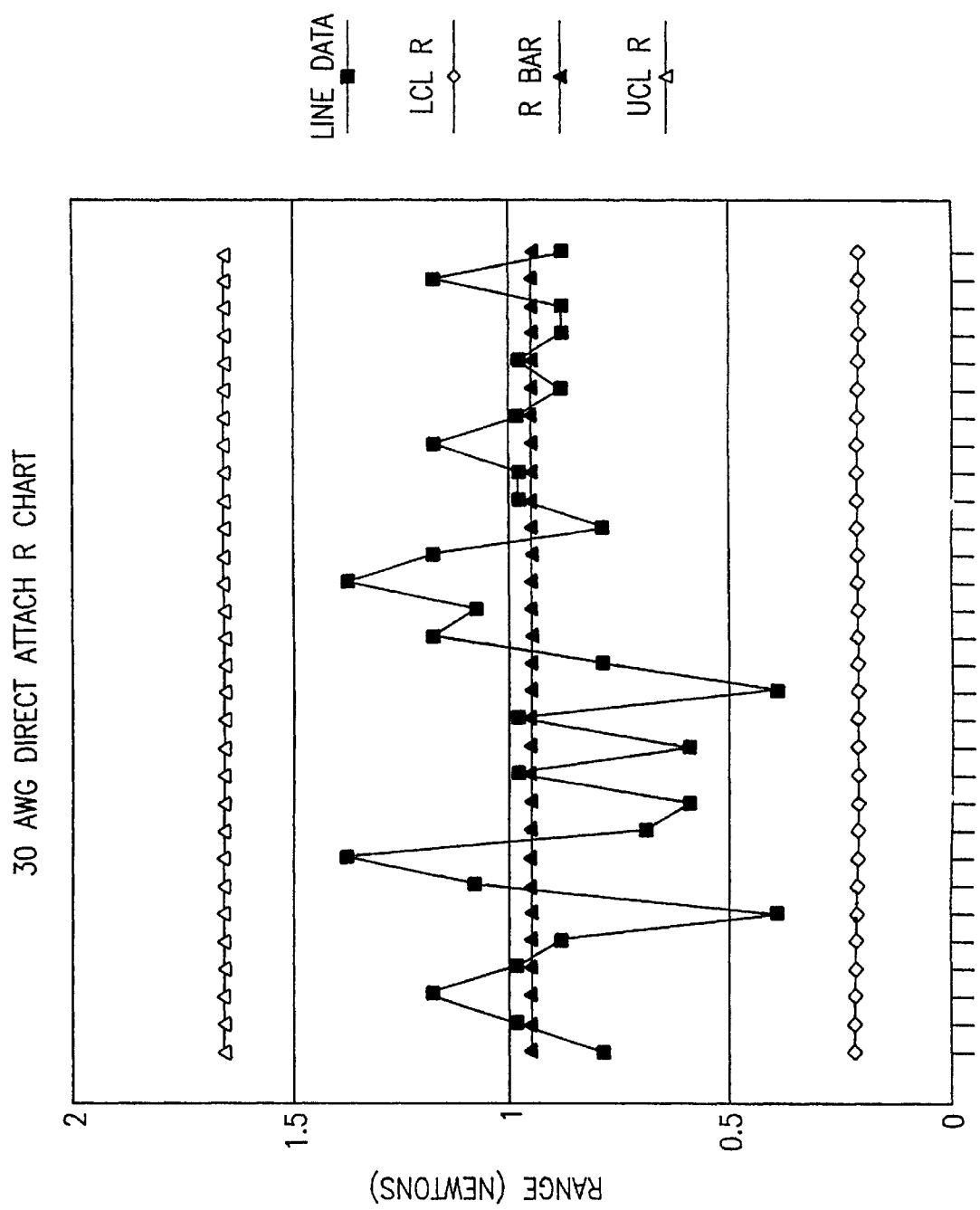
FIG. 11 is a 30 AWG direct attach Range (R) chart.

The thermocompression bonds of the present invention shown in FIG. 1 are conducted under statistical process control, which is well understood by those in the art. These techniques are described in *Process Control, Capability and Improvement: A guide to the use of control charts with an introduction to measurement system analysis and basic design of experiments for IBM training and education activities,* International Business Machines Corporation, The Quality Institute, Southbury, Conn. 06488 (1984), or *Continuing Process Control and Process Capability Improvement . . . A guide to the use of control charts for improving quality and productivity for company, supplier and dealer activities,* The Ford Motor Company (1983). In one embodiment, 10 peel tests are performed per shift. The average of the peel tests ($X^{bar}$) and Range (R) charting are made, as shown in FIG. 10 and 11. Upper and lower control limits are established for each process using standard statistical formulas. This statistical process control on the peel force provides that the desired type of bonding is continuously achieved. In the statistical process control of FIGS. 10 and 11, a batch or run of product is divided into subgroups, such as shifts. In this case, the product of interest comprises connectors having wire attached to contact/terminal leads by thermocompression bonds. In FIG. 10, $X^{double\ bar}$ is the average of all subgroup averages or the grand average of the peel tests, $X^{bar}$ is the average of the present subgroup, LCL $X^{bar}$ is the lower control limit of $X^{bar}$, and UCL $X^{bar}$ is the upper control limit of $X^{bar}$. The control limits are established above the lower specification limit to insure that even if the control limits are reached, good product is still being made. Thus, if the average of the peel test ($X^{bar}$) of the present subgroup is kept between the LCL $X^{bar}$ and the UCL $X^{bar}$, the product in the subgroup is good. FIG. 11 is a chart of the Range (R) of the peel tests. R is the difference between the maximum and the minimum peel tests. $R^{bar}$ is the average of the ranges, LCL R is the lower control limit of the range, UCL R is the upper control limit of the range, and line data are the measured values of the peel tests. In FIG. 11, the results of the peel tests are plotted with the range to insure that the line data and range stay between the LCL R and the UCL R to insure that the product is good. If the control limits are exceeded in either of FIG. 10 or 11, the product run is stopped, and the tools are modified or the electrodes cleaned before the control limits are passed. A minimum of 10 peel tests are performed after any tool modifications or electrode changes to insure that good thermocompression bonds will be made after the changes.

A method has thus been described for making and testing thermocompression bonds. The described method for making thermocompression bonds, and the described method for testing them, are exemplary only, and may be replaced by equivalents by those skilled in the art, which equivalents are intended to be covered by the attached claims.

What is claimed is:

1. A method for testing an assembly process for making direct attachment of wires to contact/terminal leads, the method comprising the following steps:

(a) aligning a wire and a contact/terminal lead between a pair of opposed electrodes such that the boundary of a portion of the wire is contained within the boundary of a portion of the contact/terminal lead, one electrode being centered on the wire portion such that there is undisturbed wire extending from both sides of said electrode;

(b) applying force through the electrodes to the wire and the contact/terminal lead such that the wire is deformed;

(c) passing electrical current through the electrodes, wire and contact/terminal lead to make a thermocompression bond of the wire to the contact/terminal lead;

(d) repeating steps a–c thereby producing at least one set of attached wires and contact/terminal leads;

(e) performing a peel test on a subgroup of each set produced in step (d);

thereby determining if the thermocompression bonds of the attached wires and contact/terminal leads produced in step (d) are acceptable.

2. The method of claim 1 wherein the deformation of step (b) is less that 50% of the outside diameter of the wire.

3. The method of claim 1 wherein the peel test comprises:

securing the contact/terminal lead;

bending the wire 90 degrees from the contact/terminal lead;

pulling the wire with a constant rate of pull until the thermocompression bonds between the wire and the contact/terminal lead breaks; and comparing the peel force required to break the thermocompression bond to a standard.

4. The method of claim 3 wherein said constant rate of pull is 50 mm per minute.

5. The method of claim 3 wherein said standard is not less than 50% of the wire tensile strength with a minimum capability index ($C_{pk}$) of 1.5, wherein the $C_{pk}$ is calculated as follows:

$$C_{pk}=(X^{double\ bar}-LSL)/3\sigma$$

where:

$X^{double\ bar}$= the average of all subgroup averages or the grand average,

LSL=a lower specification limit, and

σ=the standard deviation.

6. The method of claim 5 wherein said lower specification limit for annealed copper wire is according to the following table for the specified wire sizes:

| Wire Size (AWG) | Peel Force in Pounds | Peel Force in Newtons |
|---|---|---|
| 26 | 4 | 17.7 |
| 28 | 2.5 | 10.8 |
| 30 | 1.6 | 6.9. |

7. The method of claim 3 wherein a lower control limit average peel force (LCL $X^{bar}$) is established, and an upper control limit average peel force (UCL $X^{bar}$) is established, and the comparing step includes determining that the peel force is between the LCL $X^{bar}$ and the UCL $X^{bar}$ values.

8. The method of claim 3 wherein a lower control limit range value (LCL $R^{bar}$) is established, and an upper control limit range value (UCL $R^{bar}$) is established, wherein the range is the difference between the maximum peel force measured and the minimum peel force measured for the subgroup of peel tests, and the comparing step includes determining that the peel force is between the LCL $R^{bar}$ and the UCL $R^{bar}$ values.

9. The method of claim 1 including after step (e) the step of:

(f) performing an axial pull test of a subgroup of each set produced in step (d).

10. The method of claim 9 wherein the axial pull test comprises:

securing the contact/terminal lead;

axially pulling the wire with a constant rate of pull until the thermocompression bond between the wire and the contact/terminal lead breaks; and comparing the axial pull force required to break the thermocompression bond to a standard.

11. The method of claim 10 wherein said constant rate of pull is 50 mm per minute.

12. The method of claim 10 wherein said standard is not less than 50% of the wire tensile strength with a minimum capability index ($C_{pk}$) of 1.5, wherein the $C_{pk}$ is calculated as follows:

$$C_{pk}=(X^{double\ bar}-LSL)/3\sigma$$

where:

$X^{double\ bar}$=the average of all subgroup averages or the grand average,

LSL=a lower specification limit, and

σ=the standard deviation.

13. The method of claim 12 wherein said lower specification limit for annealed copper wire is according to the following table for the specified wire sizes:

| Wire Size (AWG) | Pull Force in Pounds | Pull Force in Newtons |
|---|---|---|
| 26 | 4 | 17.7 |
| 28 | 2.5 | 10.8 |
| 30 | 1.6 | 6.9. |

14. The method of claim 11 wherein a lower control limit average peel force (LCL $X^{bar}$) is established, and an upper control limit average axial pull force (UCL $X^{bar}$) is established, and the comparing step includes determining that the axial pull force is between the LCL $X^{bar}$ and the UCL $X^{bar}$ values.

15. The method of claim 11 wherein a lower control limit range value (LCL $R^{bar}$) is established, and an upper control limit range value (UCL $R^{bar}$) is established, wherein the range is the difference between the maximum axial pull force measured and the minimum axial pull force measured for the subgroup of axial pull tests, and the comparing step includes determining that the axial pull force is between the LCL $R^{bar}$ and the UCL $R^{bar}$ values.

16. A method of testing thermocompression bonds of wires to contact/terminal leads from at least one set of direct attachments, said method comprising:

securing each contact/terminal lead of a subgroup of the contact/terminal leads from each set;

bending the wires of the subgroup 90 degrees from the secured contact/terminal leads;

pulling the wires with a constant rate of pull until the thermocompression bonds between the wire and the contact/terminal lead breaks; and comparing the peel force required to break the thermocompression bonds to a statistically derived standard;

wherein a lower control limit average peel force (LCL $X^{bar}$) is established, and an upper control limit average peel force (UCL $X^{bar}$) is established, and the comparing step includes determining that the peel force is between the LCL $X^{bar}$ and the UCL $X^{bar}$ values.

17. The method of claim 16 wherein said constant rate of pull is 50 mm per minute.

18. The method of claim 16 wherein said standard is not less than 50% of the wire tensile a minimum capability index ($C_{pk}$) of 1.5, wherein the $C_{pk}$ is calculated as follows:

$$C_{pk} = (X^{double\ bar} - LSL)/3\sigma$$

where $X^{double\ bar}$ = the average of all subgroup averages or the grand average, LSL = a lower specification limit, and σ = the standard deviation.

19. The method of claim 18 wherein said lower specification limit for annealed copper wire is according to the following table for the specified wire sizes:

| Wire Size (AWG) | Peel Force in Pounds | Peel Force in Newtons |
|---|---|---|
| 26 | 4 | 17.7 |
| 28 | 2.5 | 10.8 |
| 30 | 1.6 | 6.9. |

20. A method of testing thermocompression bonds of wires to contact/terminal leads from at least one set of direct attachments, said method comprising:
   securing each contact/terminal lead of a subgroup of the contact/terminal leads from each set;
   bending the wires of the subgroup 90 degrees from the secured contact/terminal leads;
   pulling the wires with a constant rate of pull until the thermocompression bonds between the wire and the contact/terminal lead breaks; and
   comparing the peel force required to break the thermocompression bonds to a statistically derived standard;
   wherein a lower control limit range value (LCL $R^{bar}$) is established, and an upper control limit range value (UCL $R^{bar}$) is established, wherein the range is the difference between the maximum peel force measured and the minimum peel force measured for the subgroup of peel tests, and the comparing step includes determining that the peel force is between the LCL $R^{bar}$ and the UCL $R^{bar}$ values.

21. A method of testing thermocompression bonds of wires to contact/terminal leads from at least one set of direct attachments, said method comprising:
   securing each contact/terminal lead of a subgroup of the contact/terminal leads from each set;
   axially pulling the wires with a constant rate of pull until the thermocompression bonds between the wire and the contact/terminal lead breaks; and
   comparing the axial pull force required to break the thermocompression bonds to a statistically derived standard;
   wherein a lower control limit average peel force (LCL $X^{bar}$) is established, and an upper control limit average axial pull force (UCL $X^{bar}$) is established, and the comparing step includes determining that the axial pull force is between the LCL $X^{bar}$ and the UCL $X^{bar}$ values.

22. The method of claim 21 wherein said constant rate of pull is 50 mm per minute.

23. The method of claim 21 wherein said standard is not less than 50% of the wire tensile strength with a minimum capability index ($C_{pk}$) of 1.5, wherein the $C_{pk}$ is calculated as follows:

$$C_{pk} = (X^{double\ bar} - LSL)/3\sigma$$

where:

$X^{double\ bar}$ = the average of all subgroup averages or the grand average,

LSL = a lower specification limit, and

σ = the standard deviation.

24. The method of claim 21, wherein said lower specification limit for annealed copper wire is according to the following table for the specified wire sizes:

| Wire Size (AWG) | Pull Force in Pounds | Pull Force in Newtons |
|---|---|---|
| 26 | 4 | 17.7 |
| 28 | 2.5 | 10.8 |
| 30 | 1.6 | 6.9. |

25. A method of testing thermocompression bonds of wires to contact/terminal leads from at least one set of direct attachments, said method comprising:
   securing each contact/terminal lead of a subgroup of the contact/terminal leads from each set;
   axially pulling the wires with a constant rate of pull until the thermocompression bonds between the wire and the contact/terminal lead breaks; and
   comparing the axial pull force required to break the thermocompression bonds to a statistically derived standard;
   wherein a lower control limit range value (LCL $R^{bar}$) is established, and an upper control limit range value (UCL $R^{bar}$) is established, wherein the range is the difference between the maximum axial pull force measured and the minimum axial pull force measured for the subgroup of axial pull tests, and the comparing step includes determining that the axial pull force is between the LCL $R^{bar}$ and the UCL $R^{bar}$ values.

* * * * *

UNITED STATES PATENT AND TRADEMARK OFFICE
CERTIFICATE OF CORRECTION

PATENT NO.   : 6,520,026 B1
DATED        : February 18, 2003
INVENTOR(S)  : Lynda Anderson et al.

It is certified that error appears in the above-identified patent and that said Letters Patent is hereby corrected as shown below:

Column 7,
Line 9, "less than 50% of the wire tensile a minimum capability index" should be
-- less than 50% of the wire tensile strength with a minimum capability index --

Signed and Sealed this

Nineteenth Day of August, 2003

JAMES E. ROGAN
*Director of the United States Patent and Trademark Office*